United States Patent [19]

Freeman et al.

[11] Patent Number: 5,746,723
[45] Date of Patent: May 5, 1998

[54] CATHETER FLUID ABSORPTION DEVICE AND METHOD OF USE

[76] Inventors: Jack B. Freeman, 20 Meadow Rd., Briarcliff, N.Y. 10510; Edward R. Gomez, 317 W. 95th St. #5E, New York, N.Y. 10025

[21] Appl. No.: 600,053

[22] Filed: Feb. 12, 1996

[51] Int. Cl.⁶ .................................................... A61M 25/02
[52] U.S. Cl. ........................................ 604/178; 604/178
[58] Field of Search ............................. 604/174, 178, 604/304, 305

[56] References Cited

U.S. PATENT DOCUMENTS

| | | | |
|---|---|---|---|
| 85,995 | 1/1869 | Buffon. | |
| 3,604,426 | 9/1971 | Erikson. | |
| 3,927,672 | 12/1975 | Garcia | 128/245 |
| 4,516,968 | 5/1985 | Marshall et al. | 604/174 |
| 4,784,647 | 11/1988 | Gross | 604/178 |
| 5,100,396 | 3/1992 | Zamierowski | 604/305 |
| 5,344,415 | 9/1994 | DeBusk et al. | 604/304 |

Primary Examiner—Gary Jackson

[57] ABSTRACT

An absorbing device for use in connection with a catheter, to absorb excess liquid discharged from the meatus-catheter junction, and method of use. The device comprises a generally cylindrically shaped block of absorbing material coated with a waterproof film, the absorbing material and coating having a longitudinal bore therethrough with a slit radially directed therefrom, to facilitate mating of said device with said catheter shaft, and straps made of velcro or like material to secure the device to the catheter, and to facilitate the easy attachment and removal of the device from the catheter. The device is situated on the catheter so as not to come into contact with the body, yet close enough to the meatus-body interface so as to facilitate the transfer of liquid from the meatus-catheter junction to the device with minimal leakage. The interior of the absorbing material may be treated with a mild adhesive to prevent slippage of the device along the catheter shaft. The absorbing material may be treated an with antibacterial compound.

12 Claims, 1 Drawing Sheet

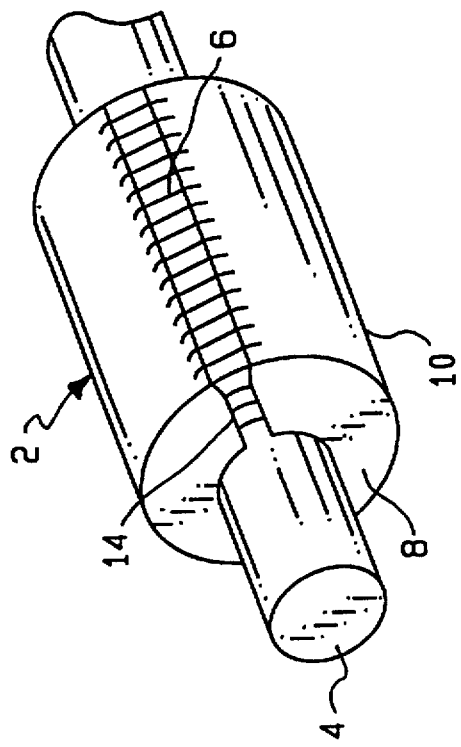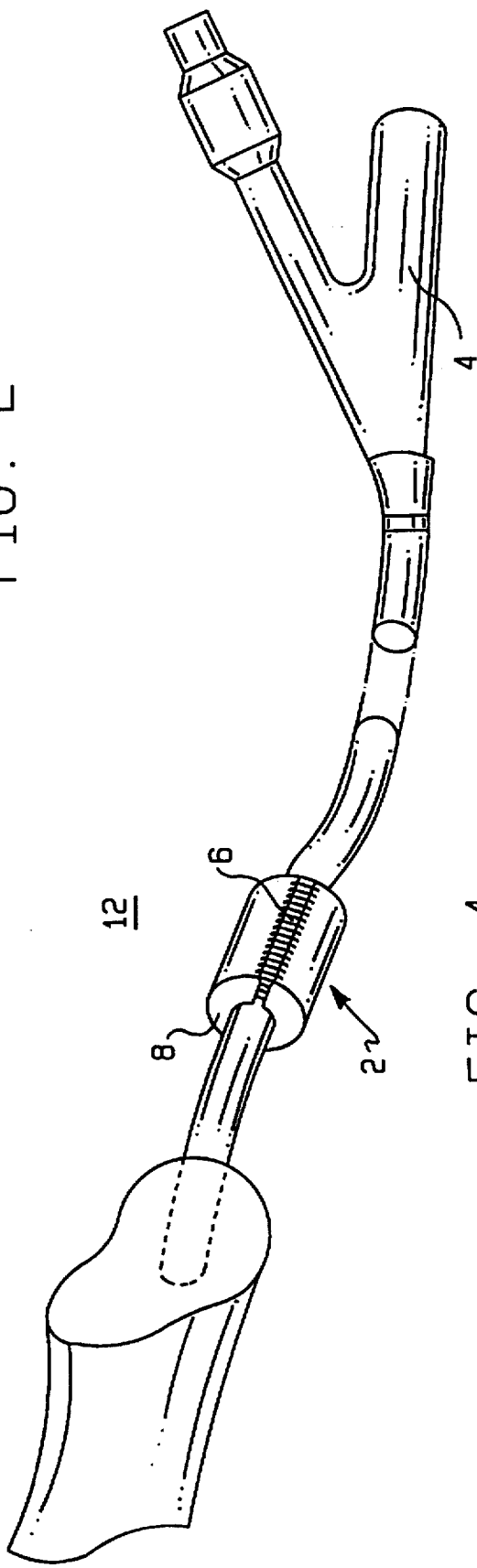

CATHETER FLUID ABSORPTION DEVICE AND METHOD OF USE

BACKGROUND OF THE INVENTION

Catheters, in general, are tubes or lines which are inserted through the skin into the body. Catheter tubes are used in a variety of medical applications. Typically, catheters are inserted into the human body for the purpose of facilitating the discharge of bodily fluids. Often, in such applications, there is leakage at the point of the meatus-catheter junction. In the case of some urinary catheters, the catheter is inserted into the penis to facilitate the discharge of urine. Leakage of urine from the junction of the penis and catheter is common in this circumstance, and may cause the patient embarrassment, by staining the patient's clothing.

The prior art in this area is concerned primarily with the prevention of infection at the meatus-catheter junction, and achieves the end of absorbing excess fluid by positioning the absorbing material directly adjacent to the patient. For example, U.S. Pat. No. 4,784,647 to Gross discloses a pad for use with a catheter for prevention of urinary tract infection, which pad is positioned on the catheter directly against the meatus of the patient. U.S. Pat. No. 3,927,672 to Garcia discloses a device which can be used with a catheter for sealing the opening to the body cavity, using tape to secure the device to the body. Similarly, U.S. Pat. No. 3,604,426 to Erickson discloses a method of applying bacteriostatic pads to urinary catheters, wherein a pad is applied to the shaft of the catheter, and kept in intimate contact with and covering the portion of the outside of the body immediately surrounding the catheter where it enters the body.

The problem common to these and other prior art devices is that the absorbing material is positioned directly against the meatus, necessarily causing the patient discomfort from the friction generated between the meatus and the absorbing material as the patient moves. This problem is compounded since often in such applications it is necessary for the patent to wear the catheter for weeks or even months at a time. In addition, many of the prior art devices are relatively complex and hence expensive to manufacture. Such complexity is necessary due to the proximity of the device adjacent to the body, since such proximity results in a closed environment for the meatus/catheter junction in which bacteria can grow. In order to address this problem, the prior art devices are necessarily designed to combat the growth of such bacteria, and to provide means to secure the device to the body at the meatus-catheter junction.

The present invention is directed to a device for absorbing leakage from the meatus-catheter junction which is inexpensive to manufacture, comfortable for the patient to wear, easily applied to the catheter, and is readily changeable. It is a further object of this invention to provide a device for absorbing leakage and which provides resistance to slippage on the catheter.

SUMMARY OF THE INVENTION

The present invention comprises a device for the absorption of excess drainage of urine and other fluids from the meatus-catheter junction, by being positioned on the catheter near but not against the meatus of the patient. The device takes advantage of the surface tension of discharged fluid to facilitate the transfer of fluid from the meatus-catheter junction to the absorbing material, thus avoiding discomfort caused by the abrasion of the absorbing material against the meatus. The device comprises an absorbing material of generally cylindrical shape made from a material which can effectively absorb liquids. The absorbing material is coated with a waterproof skin, with the exception of the area adjacent to the meatus-catheter junction, with an axial bore therethrough. The absorbing material and skin have a generally radially directed slit extending longitudinally therethrough. The slit permits the device to be opened so that the catheter can fit snugly in the bore. The invention includes a securing means which employs Velcro or like material to insure maintenance of a snug fit of the device on the catheter and to allow for easy attachment and removal of the device from the catheter. In addition, the absorbing material may be treated with an anti-bacterial agent so as to reduce the bacterial count in the area of the patient so treated. Further, a non-slip means may be included for the prevention of slippage of the device along the catheter tube. One such non-slip means is the application of a mild adhesive to all or part of the interior of the absorbing material bore.

BRIEF DESCRIPTION OF THE DRAWINGS

The objects and advantages of the present invention will become more apparent when viewed in conjunction with the following drawings, in which:

FIG. 1 is a view of the present invention disposed on a urinary catheter; and

FIG. 2 is a perspective view of the present invention.

DESCRIPTION OF THE PREFERRED EMBODIMENT

Referring to the drawings, in particular to FIG. 1, there is shown a catheter assembly 12, comprising a catheter 4, catheter fluid absorption device 2 and fastening means 6. The catheter fluid absorption device 2 is show disposed about the shaft of the catheter tube.

The device is shown more clearly in FIG. 2. The absorbing material 8 is generally cylindrically shaped and may be formed by any of a variety of fluid absorbing materials, such as foam rubber or the like. The absorbing material 8 is coated with a waterproof skin 10, with the exception of the area adjacent to the meatus-catheter junction 8. The waterproof skin 10 is formed of a flexible, resilient, waterproof material, and can be made from any of a variety of materials including polyurethane, silicone or the like. The absorbing material 8 is formed with an axial bore therethrough so as to fit snugly around the catheter 4. The absorbing material 8 and skin 10 have a generally longitudinally directed slit 14 extending generally radially outwardly from the bore. The slit 14 permits the device to be opened and manually fit around the catheter shaft, permitting easy attachment and removal of the device without removal of the catheter from the patient. Securing means, employing velcro or like material 6 are affixed to the device at the interior of the slit 14 for the purpose of securing the device to the catheter. In the manufacture of the absorbing material, a non-slip means may be included for the prevention of slippage of the device along the catheter tube. One such non-slip means is application of a mild adhesive to all or part of the interior of the absorbing material bore (not shown). The absorbing means 8 may be impregnated with an anti-bacterial agent such as povidone-iodine. The device is situated on the catheter a distance sufficient to avoid contact between the device and skin, but close enough so as to insure that all or a substantial amount of the fluid discharge is absorbed by the absorbing material 8, as in FIG. 1. The transfer of fluid from the meatus/catheter interface to the absorbing material 8 is achieved as a consequence of the surface tension of the fluid material. The location and construction of the device 12 permits the absorption of leakage from the meatus/catheter junction while causing no discomfort to the patient.

We claim:

1. A catheter and an absorbing device removably attached thereto, to minimize excess drainage from the meatus-catheter junction, comprising:

a catheter;

absorbing material at least partially surrounding said catheter, positioned on the catheter at a selected location for avoiding contact between the device and the meatus, and for insuring that a substantial amount of the drainage is absorbed by the absorbing material; and securing means for removably attaching said absorbing material to the catheter.

2. The catheter and absorbing device of claim 1, wherein said device is generally cylindrically shaped.

3. The catheter and absorbing device of claim 1, wherein said securing means comprises a hook and loop attachment.

4. The catheter and absorbing device of claim 1, wherein the absorbing material is removably attached to the catheter by an adhesive material.

5. The catheter and absorbing device of claim 1, wherein a coating is affixed to said absorbing material wherein said coating prevents fluid from leaking from said absorbing material.

6. The absorbing device of claim 5, wherein said coating comprises polyurethane.

7. The absorbing device of claim 5, wherein said coating comprises silicone.

8. The absorbing device of claim 1, wherein said securing means comprises an adhesive material affixed to said absorbing material.

9. A method of minimizing excess drainage from a meatus-catheter junction, wherein an absorbing device is used in connection with the catheter, said device comprising absorbing material at least partially surrounding the catheter and securing means detachably securing the absorbing material to the catheter comprising: positioning the device on the catheter at a selected location for avoiding contact between the device and the meatus, and for insuring that a substantial amount of the drainage is absorbed by the absorbing material; and detachably securing said device at said location.

10. The method of claim 9, wherein said securing means comprises an adhesive material for removably attaching said absorbing material.

11. The method of claim 9, wherein said securing means comprises a hook and loop attachment.

12. The method of claim 9, wherein said absorbing material comprises a coating for preventing fluid from leaking from said absorbing material.

* * * * *